United States Patent
Liu et al.

(10) Patent No.: US 11,111,332 B2
(45) Date of Patent: Sep. 7, 2021

(54) ISOCYANATE POLYMERIZATION CATALYST, PREPARATION METHOD THEREOF, AND METHOD FOR PREPARING POLYISOCYANATE BY USING SAME

(71) Applicant: Wanhua Chemical Group Co., Ltd., Shandong (CN)

(72) Inventors: Wei Liu, Shandong (CN); Yonghua Shang, Shandong (CN); Bin Shi, Shandong (CN); Yuqi Wang, Shandong (CN); Lidong Sun, Shandong (CN); Yuan Li, Shandong (CN); Weiqi Hua, Shandong (CN)

(73) Assignee: Wanhua Chemical Group Co., Ltd.

( * ) Notice: Subject to any disclaimer, the term of this patent is extended or adjusted under 35 U.S.C. 154(b) by 303 days.

(21) Appl. No.: 16/320,794

(22) PCT Filed: Aug. 16, 2016

(86) PCT No.: PCT/CN2016/095505
§ 371 (c)(1),
(2) Date: Jan. 25, 2019

(87) PCT Pub. No.: WO2018/027999
PCT Pub. Date: Feb. 15, 2018

(65) Prior Publication Data
US 2020/0123300 A1    Apr. 23, 2020

(30) Foreign Application Priority Data
Aug. 12, 2016 (CN) .......................... 201610664687.8

(51) Int. Cl.
| | |
|---|---|
| *C08G 18/20* | (2006.01) |
| *B01J 37/04* | (2006.01) |
| *C08G 18/02* | (2006.01) |
| *C08G 18/08* | (2006.01) |
| *C08G 18/18* | (2006.01) |
| *C08G 18/75* | (2006.01) |
| *C07D 235/14* | (2006.01) |
| *C07D 213/64* | (2006.01) |
| *C07D 239/36* | (2006.01) |
| *C07D 209/14* | (2006.01) |
| *C07C 211/63* | (2006.01) |
| *B01J 31/02* | (2006.01) |
| *C07D 251/30* | (2006.01) |
| *C07D 251/34* | (2006.01) |

(52) U.S. Cl.
CPC .......... *C08G 18/2063* (2013.01); *B01J 37/04* (2013.01); *C08G 18/022* (2013.01); *C08G 18/0885* (2013.01); *C08G 18/2018* (2013.01); *C08G 18/2027* (2013.01); *C08G 18/2054* (2013.01)

(58) Field of Classification Search
None
See application file for complete search history.

(56) References Cited

U.S. PATENT DOCUMENTS

| | | | |
|---|---|---|---|
| 3,211,703 | A | 10/1965 | Gilman et al. |
| 4,288,586 | A | 9/1981 | Bock et al. |
| 4,454,317 | A | 6/1984 | Disteldorf et al. |
| 6,307,102 | B1 * | 10/2001 | Tokumoto .......... C08G 18/1875 564/295 |
| 6,552,154 | B1 | 4/2003 | Kohlstruk et al. |
| 7,001,973 | B2 | 2/2006 | Kohlstruk et al. |
| 2002/0022726 | A1 | 2/2002 | Ewald et al. |

FOREIGN PATENT DOCUMENTS

| | | |
|---|---|---|
| CN | 102942525 A | 2/2013 |
| DE | 1150080 B | 6/1963 |
| DE | 102004063221 A1 | 7/2006 |
| EP | 0702000 A1 | 3/1996 |
| EP | 1170283 A1 | 1/2002 |
| GB | 837120 A | 6/1960 |
| WO | 2010054317 A2 | 5/2010 |

OTHER PUBLICATIONS

International Search Report for PCT/CN2016/095505 dated May 4, 2017.
Extended European Search Report including Written Opinion for Application No. EP16912454.2, dated Mar. 10, 2020, pp. 1-8.

* cited by examiner

*Primary Examiner* — Rachel Kahn
*Assistant Examiner* — Ha S Nguyen
(74) *Attorney, Agent, or Firm* — Lerner, David, Littenberg, Krumholz & Mentlik, LLP

(57) ABSTRACT

An isocyanate polymerization catalyst, a preparation method thereof and a method for preparing polyisocyanates comprising isocyanurate groups by using the same. The catalyst is a carboxylic acid salt containing a di-quaternary ammonium ion. The structure of the catalyst contains hydroxyl-containing aromatic heterocyclic residues. The catalyst is highly active. Only a small quantity of the catalyst is required for the polymerization of isocyanates. The prepared polyisocyanates have color values lower than 25 Hazen, monomer contents of less than 0.5% by weight, high contents of isocyanurates and low viscosities.

20 Claims, No Drawings

ISOCYANATE POLYMERIZATION CATALYST, PREPARATION METHOD THEREOF, AND METHOD FOR PREPARING POLYISOCYANATE BY USING SAME

CROSS REFERENCE TO RELATED APPLICATIONS

The present application is a national phase entry under 35 U.S.C. § 371 of International Application No. PCT/CN2016/095505, filed Aug. 16, 2016, which claims priority from Chinese Patent Application No. 201610664687.8 filed Aug. 12, 2016, all of which are hereby incorporated herein by reference.

TECHNICAL FIELD

The present invention relates to a catalyst for the polymerization of isocyanates, especially relates to a catalyst for preparing polyisocyanates comprising isocyanurate groups. And the present invention further relates to a method for preparing the catalyst, moreover, to a method for preparing polyisocyanates comprising isocyanurate groups.

TECHNICAL BACKGROUND

Isocyanurates contain a six-membered ring structure formed by the trimerization of isocyanate monomers. Polyisocyanates containing such a structure have good thermal stabilities. Particularly, aliphatic or alicyclic polyisocyanates also have anti-yellowing properties, enabling their wide applications in the fields of coatings and adhesive curing agents.

The key to the preparation of isocyanurate groups is mainly the selection of catalysts and the control of starting materials. Main catalysts include organic alkali metals and heavy metals, organophosphines, tertiary amines, quaternary ammonium bases and quaternary ammonium salts.

Patents GB837120 and U.S. Pat. No. 3,211,703 propose using organic alkali metals and heavy metals, organophosphines and tertiary amines as catalysts for the trimerization of isocyanate monomers. But in these reactions, metal catalysts are used in large amounts, they are easy to remain in the final products, and are easy to precipitate while being used, resulting in turbid products. Tertiary amine catalysts show too low reactivities at low temperatures, they only remain relatively highly active at higher temperatures, and are liable to cause odors in the products.

Patent DE1150080 proposes using quaternary ammonium bases as catalysts for the preparation of isocyanurate groups. However, under the action of such a catalyst, temperature runaway is prone to occur during the reaction process, which makes the reaction process uncontrollable. Thus, the catalysts cannot be widely used in production.

Patent U.S. Pat. No. 4,288,586 proposes an improved method, in which hydroxy substitutions are added to the cations of quaternary ammonium bases. The method can decrease the amount of heat releases from the reaction process and increase safety, but also increase the catalyst consumption and results in a relative high product color value.

Patent U.S. Pat. No. 7,001,973 discloses a benzyl substituted quaternary ammonium carboxylate catalyst. Light colored polyisocyanates are obtained by reactions catalyzed by the catalyst. With respect to the requirements of actual products, the product obtained by the reaction using the catalyst still has a relatively high color value and a viscosity that needs to be further decreased.

In the prior art, generally, the higher the content of trimers in a catalyst, the lower the viscosity and the more popular the product. If isophorone diisocyanate (IPDI) is used as an isocyanate starting material, the product generally has an isocyanurate content of 59% to 62% by weight and a viscosity of 600 to 800 cP at 25° C. If hexamethylene diisocyanate (HDI) is used as an isocyanate starting material, the product generally has an isocyanurate content of 46% to 50% by weight and a viscosity of 1000 to 1300 cP at 25° C.

Thus, there is a need to provide a novel catalyst structure for the preparation of polyisocyanates comprising isocyanurate groups. Compared with conventional products, products prepared based on this novel catalyst have low color values, low viscosities, and require less amount of catalyst.

SUMMARY OF THE INVENTION

The present invention provides a catalyst for the polymerization of isocyanates and a preparation method thereof. The catalyst can be used for the preparation of polyisocyanates comprising isocyanurate groups.

The present invention also provides a method for preparing polyisocyanates comprising isocyanurate groups using said catalyst. In specific examples, the catalyst is used in a small amount, and the polyisocyanates prepared have light colors, high isocyanurate contents, and low viscosities.

To achieve the above technical objective, the following technical solutions are used in the present invention:

A catalyst for the polymerization of isocyanates, characterized in that the catalyst has a structural formula represented by formula I:

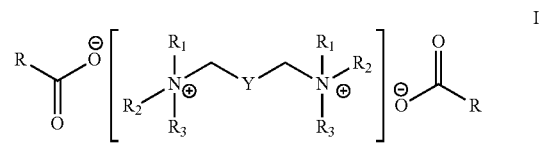

wherein, Y is a residue of a hydroxyl-containing aromatic heterocyclic compound.

Preferred catalyst is selected from the compounds of formulas II, III, IV and V:

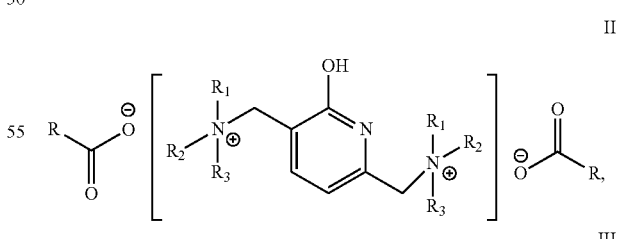

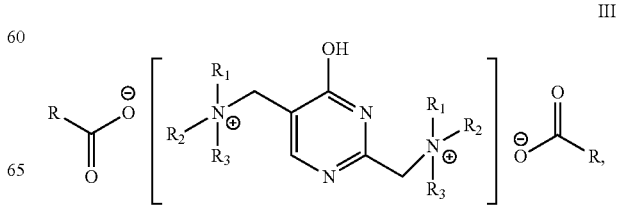

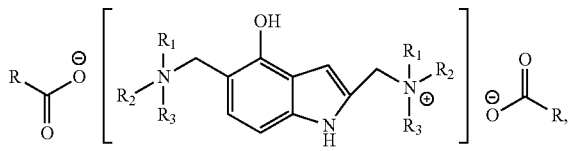

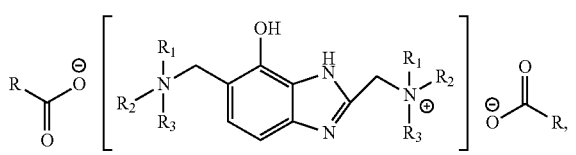

wherein, $R_1$, $R_2$ and $R_3$ are independently selected from alkyls having 1 to 20 carbon atoms, cycloalkyls having 4 to 15 carbon atoms, aralkyls having 7 to 15 carbon atoms, aryls having 6 to 15 carbon atoms, or $R_1$ and $R_2$ together form a ring structure having 4 to 6 carbon atoms, the ring structure optionally containing a N heteroatom and/or a O heteroatom; R is selected from hydrogen or alkyls having 1-10 carbon atoms.

More preferably, the catalyst is selected from the compounds of the following structural formulas:

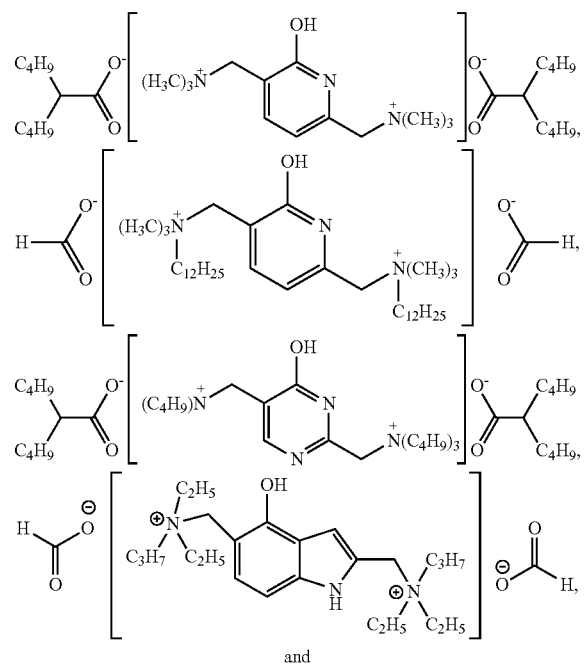

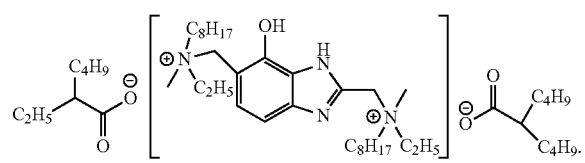

A preparation method for the catalyst according to the present invention, comprising the following steps:

(1) adding a secondary amine, formaldehyde and a hydroxyl-containing aromatic heterocyclic compound, then adding an aqueous HCl solution dropwise, then conducting a reaction at a temperature of 70-100° C.; after the completion of the reaction, allowing the system of the reaction to stand still, and to be stratified and separated to obtain an organic phase; then adding an alkyl halide to the organic phase, mixing and stirring the newly obtained mixture comprising the alkyl halide at a reaction temperature of 40-50° C. to obtain a halide containing a di-quaternary ammonium ion after the completion of the reaction;

(2) reacting a carboxylic acid with the halide containing the di-quaternary ammonium ion obtained in step (1) to obtain a carboxylic acid salt containing the di-quaternary ammonium ion.

In step (1) of the present invention, the secondary amine, formaldehyde and the hydroxyl-containing aromatic heterocyclic compound are fed in a molar ratio of (2-2.1): (2-2.1): 1.

In step (1) of the present invention, preferably an aqueous formaldehyde solution having a concentration of 20 to 50% by weight is used.

In step (1) of the present invention, the concentration of the aqueous HCl solution is 20 to 50% by weight, preferably 37% by weight.

In step (1) of the present invention, the time of the reaction of the secondary amine, formaldehyde and the hydroxyl-containing aromatic heterocyclic compound in the aqueous HCl solution is 3-6 hours.

In step (1) of the present invention, the time for stirring the mixture after the addition of the alkyl halide is 30-60 minutes.

The molar content of HCl in the aqueous HCl solution used in step (1) of the present invention is 5% to 15% of the molar amount of the hydroxyl-containing aromatic heterocyclic compound, and the concentration of the aqueous HCl solution is 20% to 50% by weight, preferably 37% by weight.

In step (1) of the present invention, the molar ratio of the alkyl halide to the secondary amine is 1:1 to 1.2:1, preferably 1:1 to 1.05:1.

The molar amount of the carboxylic acid used in step (2) of the present invention is 2 to 2.5 times, preferably 2 times of the molar amount of the hydroxyl-containing aromatic heterocyclic compound in step (1).

The temperature of the reaction of step (2) is 100 to 120° C. After step (2) of the present invention is completed, preferably organic solvents are removed by a conventional solvent removal method known in the art, such as distillation, then solvent removed solids are further purified by recrystallization to obtain purified carboxylic acid salts containing di-quaternary ammonium ions.

The secondary amine of the present invention has a structural formula represented by $NHR_1R_2$, wherein $R_1$ and $R_2$ are independently selected from alkyls having 1 to 20 carbon atoms, cycloalkyls having 4 to 15 carbon atoms, aralkyls having 7 to 15 carbon atoms, aryls having 6 to 15 carbon atoms, or $R_1$ and $R_2$ together form a ring structure having 4 to 6 carbon atoms, the ring structure optionally contains a N heteroatom and/or a O heteroatom. Preferably, $R_1$ and $R_2$ are independently selected from methyl, ethyl, propyl, butyl, octyl, dodecyl, benzyl and phenyl.

The secondary amine of the present invention is preferably dimethylamine, diethylamine, methylethylamine, dipropylamine, methylbenzylamine, dibutylamine, methylbutylamine, ethylpropylamine, ethyloctylamine, methyldodecylamine and methylphenylamine.

The alkyl halide of the present invention has a structure represented by $R_3X$, wherein $R_3$ is selected from alkyls having 1 to 20 carbon atoms, cycloalkyls having 4 to 15 carbon atoms, aralkyls having 7 to 15 carbon atoms, aryls having 6 to 15 carbon atoms, preferably methyl, ethyl, n-butyl, propyl, isobutyl, isopropyl or n-octyl, X is chlorine, bromine or iodine atom.

The alkyl halide of the present invention is more preferably selected from alkyl chlorides, suitable examples of alkyl chlorides comprising but are not limited to methyl chloride, ethyl chloride, n-butyl chloride, propyl chloride, isobutyl chloride, isopropyl chloride, n-octyl chloride and the like.

Examples of other suitable alkyl halides are n-butyl iodide and methyl bromide etc.

The carboxylic acid of the present invention has a structural formula represented by

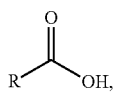

wherein R is selected from hydrogen or alkyls having 1-10 carbon atoms.

The carboxylic acid of the present invention is preferably formic acid, acetic acid, propionic acid, n-butyric acid, isobutyric acid, n-hexanoic acid, n-octanoic acid and isooctanoic acid.

The hydroxyl-containing aromatic heterocyclic compound of the present invention is a hydroxyl-substituted aromatic heterocyclic compound containing one or two nitrogen atoms or a benzo compound thereof, preferably, the hydroxyl-containing aromatic heterocyclic compound is selected from the compounds having the following structural formulas:

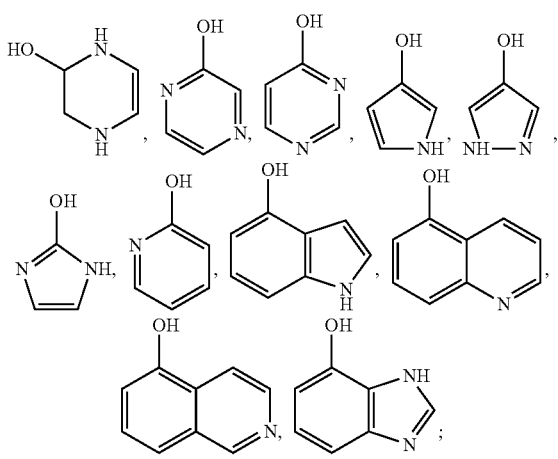

More preferably, the hydroxyl-containing aromatic heterocyclic compound is selected from the compounds having the following structural formulas: 2-hydroxypyridine

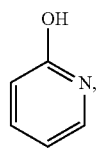

4-hydroxypyrimidine

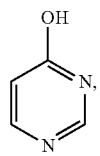

4-hydroxyindole

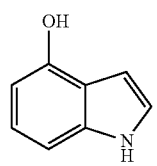

and 4-hydroxybenzimidazole

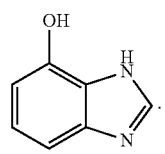

The catalyst of the present invention can be used for the catalytic preparation of polyisocyanates containing isocyanurate groups.

A method for the catalytic preparation of polyisocyanates comprising isocyanurate groups using the catalyst of the present invention, comprising the steps as follows:

under the protection of an inert gas, reacting an isocyanate starting material under the catalysis of the catalyst at a reaction temperature of 10-100° C., preferably 30-80° C. A partial trimerization takes place during the reaction process.

In principle, isocyanates that are suitable for the oligomerization process of the present invention comprise all aliphatic isocyanates. A single aliphatic isocyanate or a mixture of two or more isocyanates can be used in the present invention. All the structures or configurational isomers of isocyanates listed below are alternative examples: bis(isocyanatoalkyl)ether, propane diisocyanate, butane diisocyanate, pentane diisocyanate, hexane diisocyanate (for example, hexamethylene diisocyanate, HDI), heptane diisocyanate, octane diisocyanate (for example, octamethylene diisocyanate), nonane diisocyanate (for example, trimethyl-HDI, TMDI, usually presents as a mixture of 2,4,4- and 2,2,4-isomers) and triisocyanate (for example, 4-isocyanatomethyl-1,8-octane diisocyanate), decane diisocyanate (for example, decamethylene diisocyanate) and triisocyanate, undecane diisocyanate and triisocyanate, dodecane diisocyanate (for example, dodecamethylene diisocyanate) and triisocyanate, tetradecane diisocyanate (for example, tetradecamethylene diisocyanate), 1,4-cyclohexane diisocyanate (CHDI), 1,3- and 1,4-bis(isocyanatomethyl)cyclohexane (H$_6$XDI), 3-isocyanatomethyl-3,5,5-trimethylcyclohexyl isocyanate (isophorone diisocyanate, IPDI), 4,4'-dicyclohexylmethane diisocyanate (H$_{12}$MDI) and bis(isocyanatomethyl)norbornane (NBDI), 3 (4)-isocyanatomethyl-1-methyl-cyclohexyl isocyanate (IMCI). HDI, TMDI, 2-methylpentane- 1,5-diisocyanate (MPDI), H$_6$XDI, NBDI, IPDI and H$_{12}$MDI are preferably used.

According to the present invention, the isocyanate used for oligomerization is preferably aliphatic diisocyanate and/or alicyclic diisocyanate, more preferably hexamethylene diisocyanate (HDI), octamethylene diisocyanate, decamethylene diisocyanate, dodecamethylene diisocyanate, tetradecamethylene diisocyanate, 1,4-cyclohexane diisocyanate (CHDI), 4,4'-dicyclohexylmethane diisocyanate ($H_{12}MDI$) and isophorone diisocyanate (IPDI).

The catalyst of the present invention is used in an amount of 5-300 ppm, preferably 10-200 ppm, based on the mass of the isocyanate starting material.

The catalyst used in the method of the present invention can be used in the absence of a solvent or the catalyst can be dissolved in a solvent to form a solution to be used in the method. Solvents for dissolving the catalyst mainly comprise linear or branched monohydric alcohols and/or dihydric alcohols having 1-20 carbon atoms, the solvents optionally contain more than one hydroxyl group in the whole molecule and optionally contain other heteroatoms, preferably oxygen. Examples of the solvents for dissolving the catalyst include, but are not limited to, methanol, ethanol, 1-propanol or 2-propanol, n-butanol, isobutanol, sec-butanol, tert-butanol, n-octanol, isooctanol, heptanol, 2-ethyl-1,3-hexanediol, 1,3-butanediol or 1,4-butanediol, 1-methoxy-2-propanol, preferably ethanol, n-butanol, hexanol, heptanol and isooctanol.

When a solution of the catalyst of the present invention is used, the concentration of the solution of the catalyst is 5-50% by weight, preferably 10-30% by weight, based on the weight of the solution.

When the -NCO content in the liquid of the reaction reaches 25-26% by weight based on the weight of the liquid of the reaction, the reaction can be terminated by any prior art well known in the art, such as a high temperature treatment or adding a catalyst poison. And the temperature of the high temperature treatment is 120-150° C. with a treatment time of 0.5-1.5 hours. The catalyst poison can be selected from acids and/or derivatives thereof. Suitable examples comprise, but are not limited to one or more of phosphoric acid, benzoyl chloride, phenyl methanesulfonate, phosphates, phosphites, methylsulfonic acid, p-toluenesulfonic acid and the like. The catalyst poison is added in an equimolar amount or a slight excess amount of the catalyst.

The solution obtained after the partial trimerization is subjected to industrial conventional methods, such as thin film evaporation, extraction and rectification, to remove monomers, and the obtained polyisocyanate products have a monomer content of less than 0.5% by weight, wherein the content of isocyanurate groups is higher than that of related products in the prior art. And the products have lower viscosities and lower color values, the color values are lower than 25Hazen, even lower than 20Hazen.

If isophorone diisocyanate (IPDI) is used as an isocyanate starting material, the polyisocyanate products obtained by a catalytic synthesis using the catalyst of the present invention have an isocyanurate content of 64%-68% by weight and a viscosity of 400-600 cP at 25° C.

If hexamethylene diisocyanate (HDI) is used as an isocyanate starting material, the polyisocyanate products obtained by a catalytic synthesis using the catalyst of the present invention have an isocyanurate content of 51%-54% by weight and a viscosity of 700-900 cP at 25° C.

The obtained polyisocyanate product is in a solid or liquid state at room temperature and can be used directly or after being diluted with a solvent. The solvent can be selected from one or more of ethyl acetate, butyl acetate, xylene, methyl isoamyl ketone, propylene glycol methyl ether acetate and the like. The diluted product can have a solid content of 50-80% by weight.

The isocyanate starting material of the present invention is preferably treated with an adsorbent at 25-30° C. for 5-24 hours before conducting a polymerization reaction. And the adsorbent is used in an amount of 1-5 g adsorbent per 100 g isocyanate starting material.

The adsorbent of the present invention is selected from the group consisting of molecular sieves, activated carbon, silica gel and adsorbent resins, and a mixture of more thereof, more preferably molecular sieves and/or silica gel; the adsorbent has a particle size of 0.1-2 mm and a moisture content of <0.05% by weight.

The monomer starting material treated by the adsorption material is further filtered through a precision filter having a filter membrane with a pore size of 1-10 μm and a filter layer number of 1-3.

The beneficial effects of the preferred embodiments of the present invention lie in that the catalyst structure of the present invention contains an aromatic heterocyclic ring, which is easy to form a conjugated structure with a colored substance to reduce the concentration of the colored substance, thereby contributing to the reduction of product color values, and meanwhile increasing the content of isocyanurate groups, i.e. increasing trimer contents, thereby lowering the viscosities of products.

The starting material treated by the above-mentioned adsorbent is beneficial to reduce the amount of the catalyst used when a partial trimerization is conducted. The inventors think that maybe because the adsorbent adsorbs the acidic substance contained in the starting material, thereby contributing to the reduction of the consumption of the catalyst of the present invention.

Due to the structural characteristics of the isocyanate polymerization catalysts of the preferred embodiments of the present invention, those catalysts can reduce the consumption of the catalysts in reagent use while having relatively high catalytic activities, thereby reducing the influence of the catalyst residues on product applications. The obtained products have a high content of isocyanurates, a small amount of multimers and a monomer content of less than 0.5% by weight. The products have lower viscosities and color values lower than 25 Hazen.

EMBODIMENTS

The methods provided by the present invention will be further illustrated by the following examples, but the present invention is not limited thereby.

The content of isocyanurate groups was determined by gel chromatography (column MZ-Gel SDplus 10E3A 5 μm, 35° C., mobile phase: tetrahydrofuran, 1.0 mL/min); color values were determined by BYK color meter; the isocyanate monomer contents in reaction solutions and products were dertermined by liquid phase method; catalyst structures were characterized by NMR (Bruker DPX400) and mass spectrometry (Agilent 7890A-5975C); the viscosities of products were determined by Brookfield DV-I Prime rotor viscometer.

All the chemical reagents used in the examples were from Sigma-Aldrich, the reagents were in grade AR with purities of >99%.

EXAMPLE 1

To a synthesis kettle, dimethylamine, 37 wt % aqueous formaldehyde solution (the molar amount was calculated based on formaldehyde) and 2-hydroxypyridine were fed successively in a molar ratio of 2:1:1. 37.5 wt % aqueous HCl solution with a molar amount (the molar amount was calculated based on the amount of HCl) equal to 5% of the molar amount of 2-hydroxypyridine was then added dropwise. The temperature was increased to 80° C. to conduct a reaction, and the reaction continued for 4 hours. After the reaction was terminated, the obtained mixture was filtered, then was stewed and stratified at 25° C. to obtain an organic phase. Methyl chloride was added to the organic phase in a molar amount equal to that of dimethylamine, and the obtained system was mixed and stirred at a temperature of 40° C. for 30 minutes. Isooctanoic acid was then added in a molar amount that was twice of that of 2-hydroxypyridine. A subsequent reaction was conducted at 100° C. Hydrogen chloride gas was then distilled out. A rotary evaporator was used to remove the organic solvents in the remaining organic phase at 60° C. and an absolute pressure of 500 Pa. The remaining components were purified by recrystallization using dichloromethane/tetrahydrofuran (mass ratio: 1:1) to obtain 1 #catalyst as pale yellow crystals, 1 #catalyst was obtained in a yield of 95% based on 2-hydroxypyridine. 1 #catalyst was dissolved in ethylene glycol at a concentration of 10% by weight for later use.

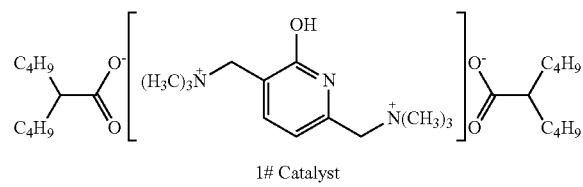

1# Catalyst

The characterization data are as follows:
$^1$H NMR (300M, TMS): δ 11.53 (s, 1H), 7.56 (s, 1H), 6.09 (s, 1H), 4.83 (s, 2H), 4.50 (s, 2H), 3.30 (m, 18H), 2.34 (d, 2H), 1.73 (d, 4H), 1.58 (d, 4H), 1.33 (d, 4H), 1.26 (d, 4H), 0.9 (d, 12H).
$^{13}$C NMR (300M, TMS): δ 179.8, 166.2, 148.1, 134.4, 126.1, 106.4, 74, 61.8, 51.7, 47.1, 30.7, 29, 22.7, 14.1, 11.3.
[M+H]$^⊕$: 526.41 (ESI)

EXAMPLE 2

To a synthesis kettle, methyldodecylamine, 37 wt % aqueous formaldehyde solution (the molar amount was calculated based on formaldehyde) and 2-hydroxypyridine were fed successively in a molar ratio of 2:2.05:1. 37.5 wt % aqueous HCl solution with a molar amount (the molar amount was calculated based on the amount of HCl) equal to 10% of the molar amount of 2-hydroxypyridine was then added dropwise. The temperature was increased to 90° C. to conduct a reaction, and the reaction continued for 4.5 hours. After the reaction was terminated, the obtained mixture was filtered, then was stewed and stratified at 30° C. to obtain an organic phase. Methyl chloride was added to the organic phase in a molar amount equal to that of methyldodecylamine, the obtained system was mixed and stirred at a temperature of 50° C. for 60 minutes and was then heated to 120° C., a subsequent reaction was conducted at that temperature. Hydrogen bromide gas and hydrogen chloride gas were then distilled out. A rotary evaporator was used to remove the organic solvents in the remaining organic phase at 60° C. and an absolute pressure of 500 Pa. The remaining components were purified by recrystallization using dichloromethane/n-hexane (mass ratio: 1:1). The products obtained by the recrystallization were dissolved in xylene, an ion exchange was carried out between the dissolved products and a basic anion resin adsorbing formic acid (DOWEX MARATHON WBA basic anion resin from Dow Company was immersed in an aqueous formic acid solution containing formic acid in a molar amount that was 2.5 times of that of 2-hydroxypyridine until no formic acid was detected in the solution), 2 #catalyst was obtained after recrystallization, 2 #catalyst was obtained in a yield of 97% based on 2-hydroxypyridine. 2 #catalyst was dissolved in propylene glycol at a concentration of 15% by weight for later use.

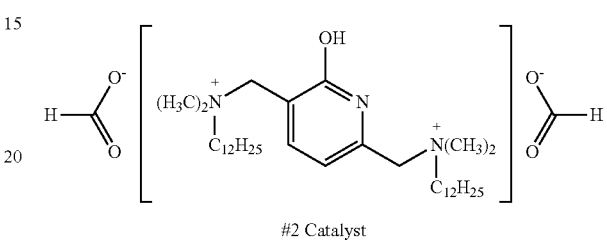

2 Catalyst

The characterization data are as follows:
$^1$H NMR (300M, TMS): δ 11.53 (s, 1H), 9.6 (d, 2H), 7.56 (s, 1H), 6.09 (s, 1H), 4.83 (s, 2H), 4.50 (s, 2H), 3.30 (m, 12H), 3.24 (d, 4H), 1.73 (d, 4H), 1.31 (d, 4H), 1.29 (m, 20H), 1.26 (m, 12H), 0.88 (d, 6H).
$^{13}$C NMR (300M, TMS): δ 169.9, 166.2, 148.1, 134.4, 126.1, 106.4, 71.8, 64.3, 59.6, 52.2, 31.9, 29.6, 26.8, 25.4, 22.7, 14.1.
[M+H]$^⊕$: 638.55 (ESI)

EXAMPLE 3

To a synthesis kettle, dibutylamine, 37 wt % aqueous formaldehyde solution (the molar amount was calculated based on formaldehyde) and 4-hydroxypyrimidine were fed successively in a molar ratio of 2.1:2:1. 37.5 wt % aqueous HCl solution with a molar amount (the molar amount was calculated based on the amount of HCl) equal to 15% of the molar amount of 4-hydroxypyrimidine was then added dropwise. The temperature was increased to 80° C. to conduct a reaction, and the reaction continued for 4 hours. After the reaction was terminated, the obtained mixture was filtered, then was stewed and stratified at room temperature to obtain an organic phase. N-butyl iodide was added to the organic phase in a molar amount equal to that of dibutylamine, and the obtained system was mixed and stirred at a temperature of 40° C. for 45 minutes. Isooctanoic acid was then added in a molar amount that was twice of that of 4-hydroxypyrimidine. A subsequent reaction was conducted at 100° C. Hydrogen chloride gas and hydrogen iodide gas were then distilled out. A rotary evaporator was used to remove the organic solvents in the remaining organic phase at 60° C. and an absolute pressure of 500 Pa. The remaining components were purified by recrystallization using dichloromethane to obtain 3 #catalyst as pale yellow crystals, 3 #catalyst was obtained in a yield of 96% based on 4-hydroxypyrimidine. 3 #catalyst was dissolved in diethylene glycol at a concentration of 20% by weight.

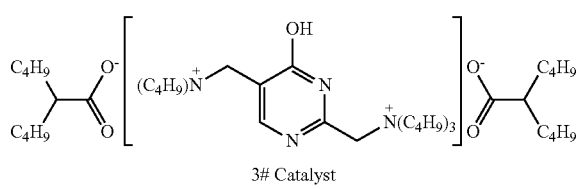

3# Catalyst

The characterization data are as follows:

$^1$H NMR (300M, TMS): δ 11.53 (s, 1H), 8.83 (s, 1H), 4.50 (d, 4H), 3.24 (m, 12H), 2.34 (s, 2H), 1.73 (m, 16H), 1.58 (d, 4H), 1.32 (m, 16H), 1.25 (d, 4H), 0.90 (m, 30H).

$^{13}$C NMR (300M, TMS): δ 179.8, 172.8, 155.7, 149.7, 123.9, 59.6, 47.1, 30.7, 29.0, 25.1, 23.5, 22.7, 19.0, 13.8, 11.3.

$[M+H]^{\oplus}$: 779.69 (ESI)

EXAMPLE 4

To a synthesis kettle, ethylpropylamine, 37 wt % aqueous formaldehyde solution (the molar amount was calculated based on formaldehyde) and 4-hydroxyindole were fed successively in a molar ratio of 2:2.1:1. 37.5 wt % aqueous HCl solution with a molar amount (the molar amount was calculated based on the amount of HCl) equal to 10% of the molar amount of 4-hydroxyindole was then added dropwise. The temperature was increased to 90° C. to conduct a reaction, and the reaction continued for 4.5 hours. After the reaction was terminated, the obtained mixture was filtered, then was stewed and stratified at 30° C. to obtain an organic phase. Ethyl chloride was added to the organic phase in a molar amount equal to that of ethylpropylamine, the obtained system was mixed and stirred at a temperature of 40° C. for 60 minutes. A subsequent reaction was conducted at 110° C. Hydrogen chloride gas was then distilled out. A rotary evaporator was used to remove the organic solvents at 50° C. and an absolute pressure of 200 Pa. The remaining components were purified by recrystallization using dichloromethane/n-hexane (mass ratio: 1:1). The products obtained by the recrystallization were dissolved in toluene, an ion exchange was carried out adequately between the dissolved products and a basic anion exchange resin adsorbing formic acid (DOWEX MARATHON WBA from Dow Company was immersed in an aqueous formic acid solution containing formic acid in a molar amount that was 2.5 times of that of 4-hydroxyindole until no formic acid was detected in the solution), 4 #catalyst was obtained after recrystallization, 4 #catalyst was obtained in a yield of 96% based on 4-hydroxyindole. 4 #catalyst was dissolved in methanol at a concentration of 25% by weight.

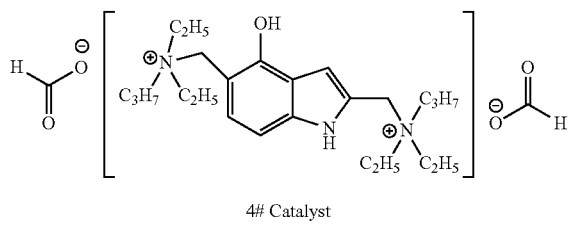

4# Catalyst

The characterization data are as follows:

$^1$H NMR (300M, TMS): δ 9.6 (s, 2H), 6.87 (s, 1H), 6.49 (s, 1H), 5.35 (s, 1H), 4.76 (d, 2H), 4.50 (d, 2H), 3.28 (m, 8H), 3.24 (d, 4H), 3.05 (d, 2H), 1.77 (d, 4H), 1.25 (m, 12H), 0.9 (m, 6H).

$^{13}$C NMR (300M, TMS): δ 169.9, 164.6, 155.7, 153.2, 128.7, 118.3, 116.8, 114.7, 65.9, 61.5, 55.7, 54.9, 53.6, 27.7, 15.7, 15.4, 11.1, 8.3, 8.0.

$[M+H]^{\oplus}$: 480.34 (ESI)

EXAMPLE 5

To a synthesis kettle, ethyloctylamine, 37 wt % aqueous formaldehyde solution (the molar amount was calculated based on formaldehyde) and 4-hydroxyl benzimidazole were fed successively in a molar ratio of 2:2:1. 37.5 wt % aqueous HCl solution with a molar amount (the molar amount was calculated based on the amount of HCl) equal to 15% of the molar amount of 4-hydroxyl benzimidazole was then added dropwise. The temperature was increased to 100° C. to conduct a reaction, and the reaction continued for 5 hours. After the reaction was terminated, the obtained mixture was filtered, then was stewed and stratified at 25° C. to obtain an organic phase. Methyl chloride was added to the organic phase in a molar amount equal to that of ethyloctylamine, and the obtained system was mixed and stirred at a temperature of 50° C. for 30 minutes. Isooctanoic acid was then added in a molar amount that was twice of that of 4-hydroxyl benzimidazole. A subsequent reaction was conducted at 120° C. Hydrogen chloride gas was then distilled out. A rotary evaporator was used to remove the organic solvents in the remaining organic phase at 60° C. and an absolute pressure of 250 Pa. The remaining components were purified by recrystallization using dichloromethane to obtain 5 #catalyst as pale yellow crystals, 5 #catalyst was obtained in a yield of 97% based on 4-hydroxyl benzimidazole. 5 #catalyst was dissolved in dipropylene glycol at a concentration of 30% by weight.

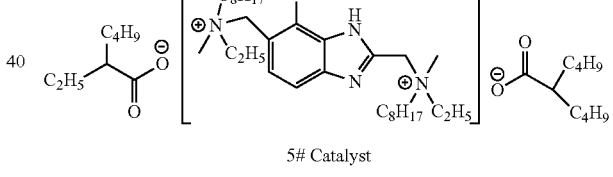

5# Catalyst

The characterization data are as follows:

$^1$H NMR (300M, TMS): δ 7.37 (s, 1H), 6.68 (s, 1H), 5.35 (s, 1H), 5.0 (s, 1H), 4.50 (d, 4H), 3.3 (m, 6H), 3.28 (d, 4H), 3.24 (d, 4H), 2.34 (d, 2H), 1.73 (m, 8H), 1.58 (d, 4H), 1.31 (m, 8H), 1.29 (m, 16H), 1.25 (m, 10H), 0.89 (m, 18H).

$^{13}$C NMR (300M, TMS): δ 179.8, 144.9, 141.5, 137.3, 134.7, 127.2, 119.3, 107.7, 61.8, 58.7, 57.1, 56.7, 47.5, 31.9, 30.7, 29.3, 26.8, 25.7, 25.1, 22.7, 14.1, 11.3, 8.0.

$[M+H]^{\oplus}$: 789.68 (ESI)

EXAMPLES 6-10

Spherical 5A molecular sieves (from Kemiou, with an effective pore size of 5 A, a silicon to aluminum ratio of 3, a particle size of 0.15 mm and a moisture content of 0.03 wt %) were immersed in the starting material IPDI at 25° C. for 12 hours, the weight ratio of the spherical 5A molecular sieves to IPDI was 3:100 before immersion, and the system obtained by IPDI and the spherical 5A molecular sieves after immersion was then filtered by a precision filter (with a double layer filter membrane having a pore size of 5 μm, from Xinkai, SC01-3-20).

800 g of treated IPDI was then placed in a 1 L round-bottom flask equipped with a reflux condenser, a stirrer, a thermometer and a nitrogen gas inlet.

The thus obtained reaction systems were heated to 60° C., and catalysts 1 #-5 #were added respectively and the catalyst-added reaction systems were continuously stirred. A rise of temperature occurred during each reaction, and the temperature of each reaction was controlled between 60-80° C. When the NCO values of the liquids of the reactions reached between 25-26% by weight, benzoyl chloride was added immediately in a molar amount equal to that of the initial catalyst, the reactions can be terminated after further stirring for 15 minutes.

Using a film evaporator (Xishanxuelang, BM 2.2) at a temperature of 180° C. and an absolute pressure of less than 200 Pa, the monomers in the reaction liquids of partial trimerizations evaporated and were removed, resulting in monomer contents less than 0.5 wt %. The obtained solid products were dissolved in butyl acetate, the content of solid components was 70 wt %.

The conditions and results of the reactions are shown in Table 1.

EXAMPLE 11

A silica gel (with a particle size of 1 mm, a moisture content of <0.05% and a moisture absorption rate of >20%, from Sinopharm) was immersed in the starting material IPDI at 30° C. for 10 hours, the weight ratio of the silica gel to IPDI was 4:100, and the system obtained by IPDI and the silica gel after immersion was then filtered by a precision filter (with a double layer filter membrane having a pore size of 5 μm).

800 g of treated IPDI was then placed in a 1 L round-bottom flask equipped with a reflux condenser, a stirrer, a thermometer and a nitrogen gas inlet.

The thus obtained reaction system was heated to 60° C., and catalyst 3 #was added and the catalyst-added system was continuously stirred. A rise of temperature occurred during the reaction, and the temperature of the reaction was controlled between 60-80° C. When the NCO value of the liquid of the reaction reached between 25-26% by weight, benzoyl chloride was added immediately in a molar amount equal to that of the initial catalyst, the reaction can be terminated after further stirring for 15 minutes.

Using a film evaporator at a temperature of 180° C. and an absolute pressure of less than 200 Pa, the monomers in the reaction liquid of a partial trimerization evaporated and were removed, resulting in a monomer content less than 0.5 wt %, thus the required product was obtained. The obtained solid product was dissolved in butyl acetate, solid component content: 70 wt %.

The conditions and results of the reaction are shown in Table 1.

EXAMPLE 12

The reaction conditions were the same as those in Example 11 except that IPDI that had not been treated by an adsorption treatment was used as the starting material and the conditions listed in Table 1 were used.

Comparative Examples 1-2:

The conditions were the same as those in Example 6 except that the catalysts were tetrabutylammonium acetate (i.e., 6 #catalyst) and tributylbenzylammonium ethylhexanoate (i.e., 7 #catalyst) respectively. The conditions and results of the reactions are shown in Table 1.

Comparative Example 3:

The conditions were the same as those in Example 12 except that the catalyst was tributylbenzylammonium ethylhexanoate (i.e., 7 #catalyst). The conditions and results of the reaction are shown in Table 1.

TABLE 1

Conditions and Results of the Reactions of Examples 6-12 and Comparative Examples 1-3

| Serial Number | Example | | | | | | | Comparative Example | | |
|---|---|---|---|---|---|---|---|---|---|---|
| | 6 | 7 | 8 | 9 | 10 | 11 | 12 | 1 | 2 | 3 |
| Catalyst | 1# | 2# | 3# | 4# | 5# | 3# | 3# | 6# | 7# | 7# |
| Amount of Catalyst/ppm | 30 | 70 | 80 | 85 | 95 | 85 | 130 | 200 | 250 | 350 |
| NCO content of Reaction Liquid/wt % | 25.1 | 25.3 | 25.2 | 25.5 | 25.4 | 25.8 | 25.8 | 25.6 | 25.4 | 25.8 |
| Content of Isocyanurate/wt % | 68 | 67 | 66 | 66 | 65 | 64 | 64 | 61 | 60 | 59 |
| Color value of Product/Hazen | 9 | 15 | 15 | 18 | 24 | 11 | 17 | 40 | 45 | 50 |
| Viscosity of Product/25° C., cP | 400 | 420 | 450 | 445 | 480 | 500 | 550 | 700 | 740 | 800 |
| Monomer Content of Product/wt % | 0.2 | 0.3 | 0.25 | 0.2 | 0.3 | 0.25 | 0.30 | 0.3 | 0.2 | 0.30 |

Compared with the comparative examples, when the catalysts of the present invention were used for IPDI trimerization, the obtained polyisocyanates have higher contents of isocyanurate, lower product color values. Under the same reaction conditions, the trimerizations using an isocyanate starting material treated with an adsorbent require a smaller amount of catalyst, and the obtained products have lower color values.

EXAMPLES 13-15

Spherical 5A molecular sieves (from Kemiou, with an effective pore size of 6 Å, a silicon to aluminum ratio of 3.5, a particle size of 0.25 mm and a moisture content of 0.04 wt %) were immersed in the starting material HDI at 25° C. for 15 hours, the weight ratio of the spherical 5A molecular sieves to HDI was 3.5:100 after immersion, and the system obtained by HDI and the spherical 5A molecular sieves after immersion was then filtered by a precision filter (with a triple layer filter membrane having a pore size of 10 μm, from Xinkai, SC01-3-20).

1000 g of treated HDI was then placed in a 1 L four-necked round-bottom flask equipped with a reflux condenser, a stirrer, a thermometer and a nitrogen gas inlet.

The starting material HDI was heated to 35° C., and catalysts 1 #, 3 # and 5 # were added respectively and the obtained reaction systems were continuously stirred. A rise of temperature occurred during each reaction, and the temperature of each reaction was controlled between 45-55° C. When the NCO values of the liquids of the reactions reached between 25-26% by weight based on the weights of the liquids of the reactions, phosphoric acid was added immediately in a molar amount equal to that of each catalyst, the reactions can be terminated after further stirring for 15 minutes.

Using a film evaporator at a temperature of 150° C. and an absolute pressure of less than 100 Pa, the monomers in the reaction liquids of partial trimerizations evaporated and were removed, resulting in monomer contents less than 0.5 wt %, thus the required products were obtained.

The conditions and results of the reactions are shown in Table 2.

EXAMPLE 16

A silica gel (with a particle size of 0.5 mm, a moisture content of 0.04 wt %, a moisture absorption rate of >20%, from Sinopharm) was immersed in the starting material HDI at 30° C. for 10 hours, the weight ratio of the silica gel to HDI was 5:100, and the system obtained by HDI and the silica gel after immersion was then filtered by a precision filter (with a double layer filter membrane having a pore size of 5 μmm).

The reaction conditions were the same as those in Example 13 except that 2 #catalyst was used as the catalyst and the conditions listed in Table 2 were used.

EXAMPLE 17

The reaction conditions were the same as those in Example 13 except that HDI that had not been treated by an adsorption treatment was used as the starting material and the conditions listed in Table 2 were used.

COMPARATIVE EXAMPLES 4-5:

The conditions were the same as those in Example 13 except that the catalysts were tetrabutylammonium acetate (i.e., 6 #catalyst) and tributylbenzylammonium ethylhexanoate (i.e., 7 #catalyst) respectively. The conditions and results of the reactions are shown in Table 2.

COMPARATIVE EXAMPLE 6

The conditions were the same as those in Example 17 except that the catalyst was tributylbenzylammonium ethylhexanoate (i.e., 7 #catalyst). The conditions and results of the reaction are shown in Table 2.

TABLE 2

Conditions and Results of the Reactions of Examples 13-17 and Comparative Examples 4-6

| | Example | | | | | Comparative Example | | |
|---|---|---|---|---|---|---|---|---|
| | 13 | 14 | 15 | 16 | 17 | 4 | 5 | 6 |
| Catalyst | 1# | 3# | 5# | 2# | 2# | 6# | 7# | 7# |
| Amount of Catalyst/ppm | 40 | 70 | 30 | 90 | 100 | 200 | 280 | 400 |
| NCO content of Reaction Liquid/wt % | 25.2 | 25.4 | 25.6 | 25.3 | 25.4 | 25.1 | 25.4 | 25.2 |
| Content of Isocyanurate/wt % | 54 | 53 | 52 | 52 | 51 | 49 | 48 | 46 |
| Color value of Product/Hazen | 12 | 18 | 25 | 20 | 24 | 38 | 47 | 55 |
| Viscosity of Product/25° C., cP | 700 | 750 | 800 | 800 | 850 | 1000 | 1100 | 1300 |
| Monomer Content of Product/wt % | 0.25 | 0.3 | 0.2 | 0.25 | 0.3 | 0.4 | 0.3 | 0.25 |

Compared with the comparative examples, when the HDI trimer products were obtained by using the catalysts of the present invention, the catalyst consumptions were less, the contents of isocyanurate groups in the products were higher, and the product color values were lower. Under the same reaction conditions, the trimerizations using isocyanate starting materials treated with adsorbents require fewer amounts of the catalysts, and products having lower color values were obtained.

The invention claimed is:

1. A catalyst for the polymerization of isocyanates, wherein the catalyst has a structural formula represented by formula I:

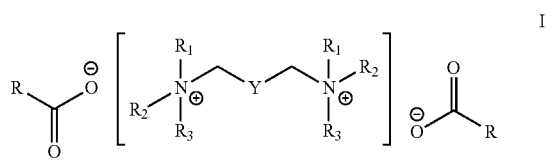

wherein, Y is a residue of a hydroxyl-containing aromatic heterocyclic compound;

wherein, $R_1$, $R_2$ and $R_3$ are independently selected from alkyls having 1-20 carbon atoms, cycloalkyls having 4-15 carbon atoms, aralkyls having 7-15 carbon atoms, aryls having 6-15 carbon atoms, or $R_1$ and $R_2$ together form a ring structure having 4-6 carbon atoms, the ring structure formed by $R_1$ and $R_2$ optionally contains a N heteroatom and/or a O heteroatom in the ring structure; and R is selected from hydrogen or alkyls having 1-10 carbon atoms.

2. The catalyst according to claim 1, wherein the catalyst is selected from the compounds of formulas II, III, IV and V:

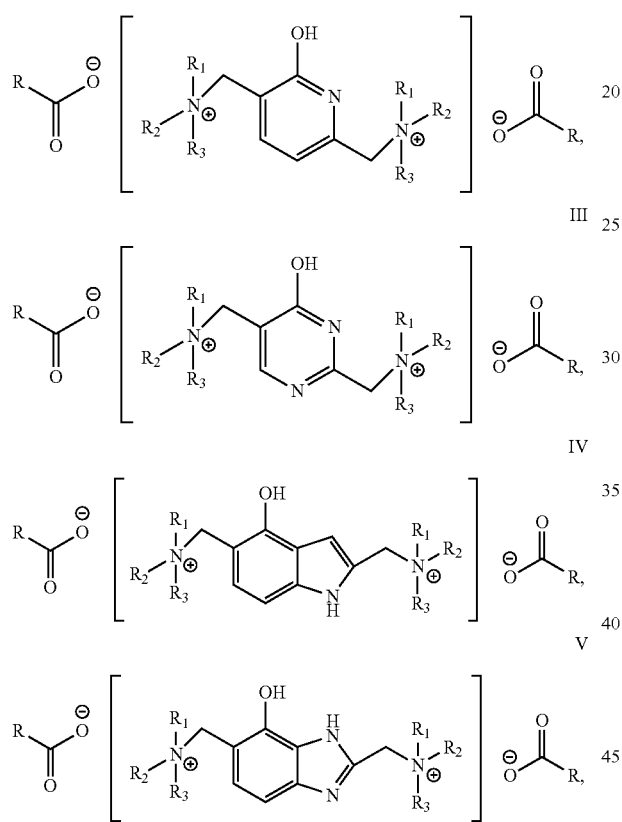

3. The catalyst according to claim 1, wherein the catalyst is selected from the compounds of the following structural formulas:

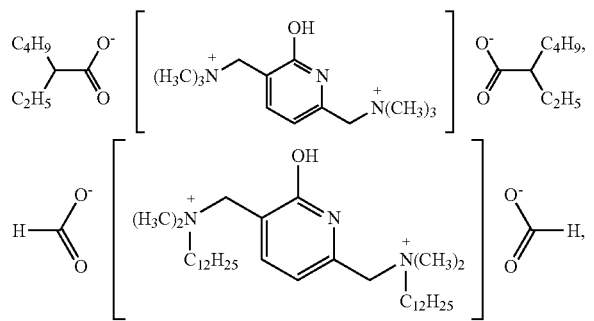

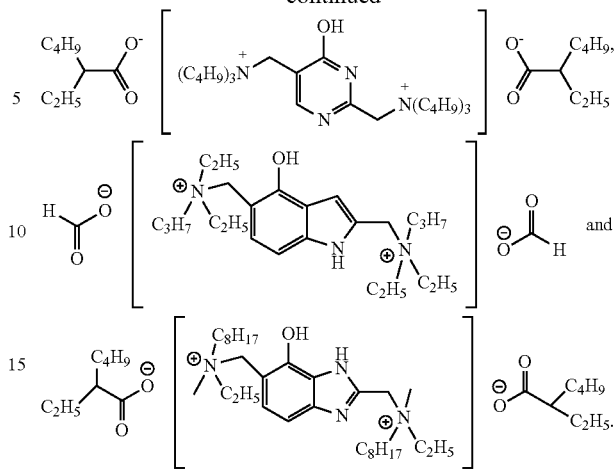

4. A preparation method for the catalyst having the structural formula represented by formula I according to claim 1, comprising the following steps:
  (1) adding a secondary amine, formaldehyde and a hydroxyl-containing aromatic heterocyclic compound, then adding an aqueous HCl solution dropwise, then conducting a reaction at a temperature of 70-100° C.; after the completion of the reaction, allowing the system of the reaction to stand still, and to be stratified and separated to obtain an organic phase; then adding an alkyl halide to the organic phase, mixing and stirring the newly obtained mixture comprising the alkyl halide at a reaction temperature of 40-50° C. to obtain a halide containing a di-quaternary ammonium ion after the completion of the reaction;
  (2) reacting a carboxylic acid with the halide containing the di-quaternary ammonium ion obtained in step (1) to obtain a carboxylic acid salt containing the di-quaternary ammonium ion.

5. The preparation method according to claim 4, wherein in step (1), the secondary amine, formaldehyde and hydroxyl-containing aromatic heterocyclic compound are fed in a molar ratio of (2-2.1): (2-2.1):1; the formaldehyde is used as an aqueous formaldehyde solution having a concentration of 20%-50% by weight.

6. The preparation method according to claim 4, wherein the molar content of HCl in the aqueous HCl solution used in step (1) is 5%-15% of the molar amount of the hydroxyl-containing aromatic heterocyclic compound, and the concentration of the aqueous HCl solution is 20%-50% by weight, the molar ratio of the alkyl halide to the secondary amine is (1-1.2):1.

7. The preparation method according to claim 4, wherein the molar amount of the carboxylic acid used in step (2) is 2-2.5 times, of the molar amount of the hydroxyl-containing aromatic heterocyclic compound in step (1).

8. The preparation method according to claim 4, wherein the temperature of the reaction of step (2) is 100-120° C.

9. The preparation method according to claim 4, wherein the secondary amine has a structural formula represented by $NHR_1R_2$, wherein $R_1$ and $R_2$ are independently selected from alkyls having 1-20 carbon atoms, cycloalkyls having 4-15 carbon atoms, aralkyls having 7-15 carbon atoms, aryls having 6-15 carbon atoms, or $R_1$ and $R_2$ together form a ring structure having 4-6 carbon atoms, and the ring structure formed by $R_1$ and $R_2$ optionally contains a N heteroatom and/or a O heteroatom.

10. The preparation method according to claim 4, wherein the alkyl halide has a structure represented by $R_3X$, wherein $R_3$ is selected from alkyls having 1-20 carbon atoms, cycloalkyls having 4-15 carbon atoms, aralkyls having 7-15 carbon atoms, and aryls having 6-15 carbon atoms, and wherein X is chlorine, bromine or iodine atom.

11. The preparation method according to claim 4, wherein the

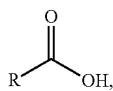

carboxylic acid has a structural formula represented by wherein R is selected from hydrogen or alkyls having 1-10 carbon atoms.

12. The preparation method according to claim 4, wherein the hydroxyl-containing aromatic heterocyclic compound is a hydroxyl-substituted aromatic heterocyclic compound containing one or two nitrogen atoms.

13. A method for preparing polyisocyanates comprising isocyanurate groups using the catalyst according to claim 1, comprising the steps as follows:
    under the protection of an inert gas, reacting an isocyanate starting material under the catalysis of the catalyst at a reaction temperature of 10-100° C.

14. The method according to claim 13, wherein the catalyst is used in an amount of 5-300 ppm based on the mass of the isocyanate starting material.

15. The method according to claim 13, wherein the isocyanate starting material is treated with an adsorbent before conducting a polymerization reaction.

16. The method according to claim 15, wherein the isocyanate starting material is treated with the adsorbent at 25-30° C. for 5-24 hours; the adsorbent is used in an amount of 1-5 g adsorbent per 100 g isocyanate starting material; the adsorbent is selected from the group consisting of molecular sieves, activated carbon, silica gel and adsorbent resins, and a mixture of more thereof, and the adsorbent has a particle size of 0.1-2 mm and a moisture content of <0.05% by weight.

17. The preparation method according to claim 4, wherein the molar content of HCl in the aqueous HCl solution used in step (1) is 5%-15% of the molar amount of the hydroxyl-containing aromatic heterocyclic compound, and the concentration of the aqueous HCl solution is 20%-50% by weight, the molar ratio of the alkyl halide to the secondary amine is (1-1.05):1; and the molar amount of the carboxylic acid used in step (2) is 2 times of the molar amount of the hydroxyl-containing aromatic heterocyclic compound in step (1).

18. The preparation method according to claim 4, wherein the secondary amine has a structural formula represented by $NHR_1R_2$, wherein $R_1$ and $R_2$ are independently selected from methyl, ethyl, propyl, butyl, octyl, dodecyl, benzyl and phenyl; the secondary amine is dimethylamine, diethylamine, methylethylamine, dipropylamine, methylbenzylamine, dibutylamine, methylbutylamine, ethylpropylamine, ethyloctylamine, methyldodecylamine or methylphenylamine;
    wherein the alkyl halide is selected from methyl chloride, ethyl chloride, n-butyl chloride, propyl chloride, isobutyl chloride, isopropyl chloride, n-octyl chloride, n-butyl iodide and methyl bromide;
    wherein the carboxylic acid is selected from formic acid, acetic acid, propionic acid, n-butyric acid, isobutyric acid, n-hexanoic acid, n-octanoic acid and isooctanoic acid; and
    the hydroxyl-containing aromatic heterocyclic compound is selected from the compounds having the following structural formulas:

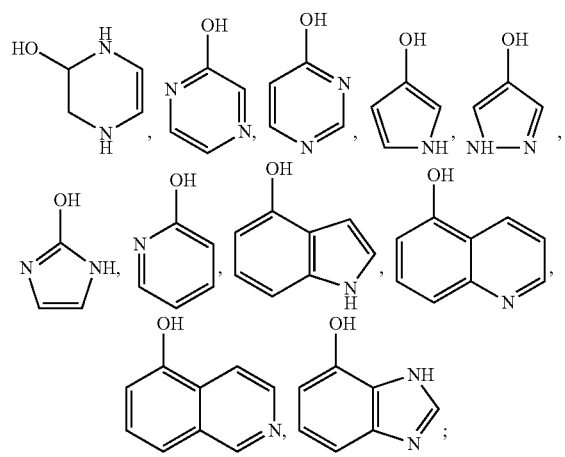

19. The preparation method according to claim 4, wherein the hydroxyl-containing aromatic heterocyclic compound is selected from the compounds having the following structural formulas:

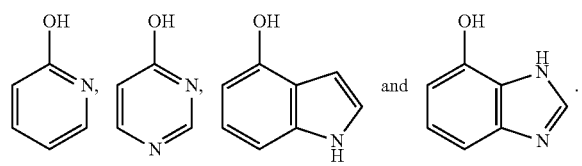

20. The method according to claim 13, wherein the reaction temperature is 30-80° C.; and
    the catalyst is used in an amount of 10-200 ppm based on the mass of the isocyanate starting material.

* * * * *